(12) United States Patent
Ishii et al.

(10) Patent No.: US 11,900,513 B2
(45) Date of Patent: Feb. 13, 2024

(54) MEDICAL IMAGE DISPLAY APPARATUS

(71) Applicant: CANON MEDICAL SYSTEMS CORPORATION, Otawara (JP)

(72) Inventors: Hideaki Ishii, Nasushiobara (JP); Guang Yi Ong, Nasushiobara (JP); Hiroshizu Morishima, Utsunomiya (JP); Junya Suzuki, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/818,043

(22) Filed: Aug. 8, 2022

(65) Prior Publication Data
US 2023/0066028 A1    Mar. 2, 2023

(30) Foreign Application Priority Data
Aug. 26, 2021   (JP) .................... 2021-138245

(51) Int. Cl.
*G16H 30/20* (2018.01)
*G06T 11/60* (2006.01)
*G06T 5/50* (2006.01)
*G06T 7/00* (2017.01)
*G16H 30/40* (2018.01)
*G06F 3/0482* (2013.01)

(52) U.S. Cl.
CPC ............ *G06T 11/60* (2013.01); *G06F 3/0482* (2013.01); *G06T 5/50* (2013.01); *G06T 7/0012* (2013.01); *G16H 30/40* (2018.01); *G06T 2200/24* (2013.01); *G06T 2207/30004* (2013.01)

(58) Field of Classification Search
CPC ......... G06T 11/60; G06T 5/50; G06T 7/0012; G06T 2200/24; G06T 2207/30004; G06F 3/0482; G16H 30/40
See application file for complete search history.

(56) References Cited

U.S. PATENT DOCUMENTS

| | | | |
|---|---|---|---|
| 9,471,747 B2 * | 10/2016 | Shrestha | G16H 10/60 |
| 10,127,662 B1 * | 11/2018 | Reicher | G06T 7/30 |
| 10,268,802 B2 | 4/2019 | Yanagida et al. | |
| 10,884,593 B1 * | 1/2021 | Jimenez | G06F 3/147 |
| 2006/0050943 A1 * | 3/2006 | Ozaki | A61B 6/465 |
| | | | 382/131 |

(Continued)

FOREIGN PATENT DOCUMENTS

JP    2015-186567 A    10/2015

*Primary Examiner* — Hien L Duong
(74) *Attorney, Agent, or Firm* — Oblon, McClelland, Maier & Neustadt, L.L.P.

(57) ABSTRACT

A medical image display apparatus according to an embodiment includes processing circuitry. The processing circuitry is configured to: identify imaged ranges respectively corresponding to a plurality of examinations, on the basis of anatomical information from a plurality of medical images taken of an examined subject in the plurality of examinations; map the imaged ranges respectively corresponding to the plurality of examinations onto a single human body model; and cause a display unit to display a list of information about the plurality of examinations and the human body model on which the imaged ranges respectively corresponding to the plurality of examinations are mapped, so as to be kept in correspondence with each other.

8 Claims, 12 Drawing Sheets

(56) References Cited

U.S. PATENT DOCUMENTS

| | | | |
|---|---|---|---|
| 2012/0050330 A1* | 3/2012 | Iizuka | G16H 30/20 345/641 |
| 2013/0035957 A1* | 2/2013 | Gossler | A61B 5/055 705/3 |
| 2013/0111387 A1* | 5/2013 | Li | G16H 10/60 715/771 |
| 2015/0261915 A1* | 9/2015 | Yanagida | G06F 40/169 382/131 |
| 2016/0307315 A1* | 10/2016 | Segawa | B33Y 50/02 |
| 2021/0124465 A1* | 4/2021 | Sahu | G06F 3/0482 |

* cited by examiner

MEDICAL IMAGE DISPLAY APPARATUS

CROSS-REFERENCE TO RELATED APPLICATIONS

This application is based upon and claims the benefit of priority from Japanese Patent Application No. 2021-138245, filed on Aug. 26, 2021; the entire contents of which are incorporated herein by reference.

FIELD

Embodiments described herein relate generally to a medical image display apparatus.

BACKGROUND

One of the problems to be solved by the embodiments disclosed in the present specification and drawings is to enable users to easily understand and compare imaged ranges corresponding to various medical examinations (hereinafter, "examinations") performed on an examined subject. However, problems to be solved by the embodiments disclosed in the present specification and drawings are not limited to the abovementioned problem. It is also possible to consider problems corresponding to advantageous effects achieved by the configurations in the embodiments described below as other problems.

DETAILED DESCRIPTION

Exemplary embodiments of a medical image display apparatus will be explained in detail below, with reference to the accompanying drawings.

First Embodiment

Figure 1:
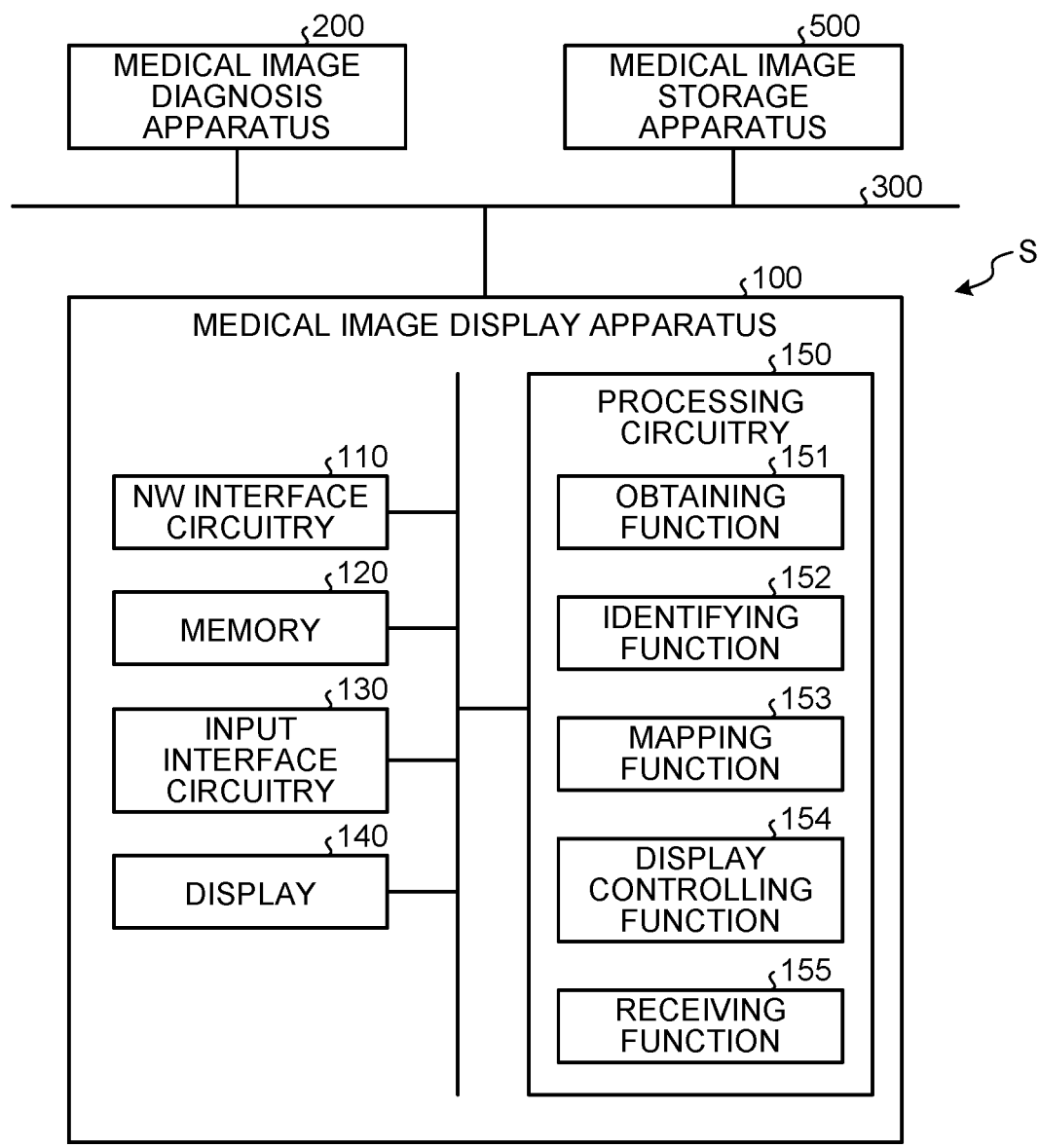
FIG. 1 is a diagram illustrating an example of an overall configuration of a medical image processing system according to a first embodiment.

FIG. 1 is a block diagram illustrating an exemplary configuration of a medical image processing system S according to a first embodiment. As illustrated in FIG. 1, the medical image processing system S includes a medical image display apparatus 100, a medical image diagnosis apparatus 200, and a medical image storage apparatus 500. The medical image display apparatus 100 is communicably connected to the medical image storage apparatus 500 via a network 300 such as an intra-hospital Local Area Network (LAN).

The medical image storage apparatus 500 is configured to store therein medical images taken by the medical image diagnosis apparatus 200. The medical image storage apparatus 500 is, for example, a server apparatus in a Picture Archiving and Communication System (PACS) and is configured to store therein the medical images in a format compliant with Digital imaging and Communications in Medicine (DICOM). The medical images are, for example, Computed Tomography (CT) image data, magnetic resonance image data, ultrasound diagnosis image data, and/or the like, but are not limited to these examples. For example, the medical image storage apparatus 500 is realized by using a computer device such as a Database (DB) server and is configured to store the data of the medical images into a semiconductor memory element such as a Random Access memory (RAM) or a flash memory, or a storage circuit such as a hard disk or an optical disk.

For example, the medical image diagnosis apparatus 200 is an apparatus configured to take medical images of an examined subject (hereinafter, "patient") and may be a Magnetic Resonance Imaging (MRI) apparatus, an X-ray Computed Tomography (CT) apparatus, an X-ray diagnosis apparatus, an ultrasound diagnosis apparatus, a Positron Emission Tomography (PET) apparatus, or a Single Photon Emission Computed Tomography (SPECT) apparatus; however, possible examples are not limited to these. The medical image diagnosis apparatus 200 may be referred to as a modality. Further, although FIG. 1 illustrates the single medical image diagnosis apparatus 200, two or more medical image diagnosis apparatuses 200 may be provided.

The medical images are images taken of the patient by the medical image diagnosis apparatus 200. For example, the medical images may be magnetic resonance images, X-ray CT images, and/or the like; however, possible examples are not limited to these.

For example, the medical image display apparatus 100 is an information processing apparatus such as a server apparatus or a Personal Computer (PC) and includes Network (NW) interface circuitry 110, a memory 120, input interface circuitry 130, a display 140, and processing circuitry 150.

The NW interface circuitry 110 is connected to the processing circuitry 150 and is configured to control various types of data transfer and communication performed among the medical image display apparatus 100, the medical image diagnosis apparatus 200, and the medical image storage apparatus 500. The NW interface circuitry 110 is realized by using a network card, a network adaptor, a Network Interface Controller (NIC), or the like.

The memory 120 is configured to store therein, in advance, various types of information used by the processing circuitry 150. Further, the memory 120 is configured to store therein various types of programs. For example, the memory 120 is a storage device, such as a Hard Disk Drive (HDD), a Solid State Drive (SSD), or an integrated circuit storage device, configured to store therein various types of information. Further, instead of being an HDD or an SSD, the memory 120 may be a drive device configured to read and write various types of information from and to a portable storage medium such as a Compact Disc (CD), a Digital Versatile Disc (DVD), or a flash memory, or a semiconductor memory element such as a Random Access Memory (RAM).

The input interface circuitry 130 is realized by using a trackball, a switch button, a mouse, a keyboard, a touchpad on which input operations can be performed by touching an operation surface thereof, a touch screen in which a display screen and a touchpad are integrally formed, a contactless input circuit using an optical sensor, an audio input circuit, and/or the like configured to receive operations from a user. The input interface circuitry 130 is connected to the processing circuitry 150 and is configured to convert the input operations received from the user into electrical signals and to output the electrical signals to the processing circuitry 150. In the present disclosure, the input interface does not necessarily have to include physical operation component parts such as a mouse, a keyboard, and/or the like. For instance, possible examples of the input interface include an electrical signal processing circuit configured to receive an electrical signal corresponding to an input operation from an external input device provided separately from the apparatus and to output the electrical signal to the processing circuitry 150.

The display 140 is configured to display various types of information under control of the processing circuitry 150. For example, the display 140 is configured to output the image interpretation viewer including any of medical images generated by the processing circuitry 150, a Graphical User Interface (GUI) used for receiving various types of operations from the user, and the like. The display 140 is an example of a display unit.

More specifically, the display 140 may be a liquid crystal display device, a Cathode Ray Tube (CRT) display device, or the like. In an example, the input interface circuitry 130 and the display 140 may be integrally formed. For example, the input interface circuitry 130 and the display 140 may be realized by using a touch panel.

The processing circuitry 150 is a processor configured to realize functions corresponding to the programs, by reading and executing the programs from the memory 120. The processing circuitry 150 according to the present embodiment includes an obtaining function 151, an identifying function 152, a mapping function 153, a display controlling function 154, and a receiving function 155. The obtaining function 151 is an example of an obtaining unit. The identifying function 152 is an example of an identifying unit. The mapping function 153 is an example of a mapping unit. The display controlling function 154 is an example of a display controlling unit. The receiving function 155 is an example of a receiving unit.

In this situation, for example, processing functions of constituent elements of the processing circuitry 150, namely, the obtaining function 151, the identifying function 152, the mapping function 153, the display controlling function 154, and the receiving function 155, are stored in the memory 120 in the form of computer-executable programs. The processing circuitry 150 is a processor. For example, the processing circuitry 150 is configured to realize the functions corresponding to the programs, by reading and executing the programs from the memory 120. In other words, the processing circuitry 150 that has read the programs has the functions illustrated within the processing circuitry 150 in FIG. 1. Further, although the example was explained with reference to FIG. 1 in which the single processor realizes the processing functions implemented by the obtaining function 151, the identifying function 152, the mapping function 153, the display controlling function 154, and the receiving function 155, it is also acceptable to structure the processing circuitry 150 by combining together a plurality of independent circuits, so as to realize the functions as a result of the processors executing the programs. Further, although the example was explained with reference to FIG. 1 in which the single storage circuit (i.e., the memory 120) has stored therein the programs corresponding to the processing functions, it is also acceptable to arrange a plurality of storage circuits in a distributed manner, so that the processing circuitry 150 reads a corresponding program from each of the individual storage circuits.

In the above description, the example was explained in which the one or more "processors" are configured to read and execute the programs corresponding to the functions from the storage circuit; however, possible embodiments are not limited to this example. The term "processor" denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processors are each a CPU, for example, the processors are configured to realize the functions by reading and executing the programs saved in a storage circuit. Alternatively, when the processors are each an ASIC, instead of having the programs saved in the memory 120, the functions are directly incorporated into the circuits of the processors as logic circuits. Further, the processors according to the present embodiments do not each necessarily have to be structured as a single circuit. It is also acceptable to structure one processor by combining together a plurality of independent circuits, so as to realize the functions thereof. Further, two or more of the constituent elements in FIG. 1 may be integrated together in a single processor so as to realize the functions thereof.

From the medical image storage apparatus 500 via the network 300 and the NW interface circuitry 110, the obtaining function 151 is configured to obtain a plurality of medical images taken of the patient in a plurality of examinations. Alternatively, the obtaining function 151 may obtain the medical images from the medical image diagnosis apparatus 200.

The plurality of medical images obtained by the obtaining function 151 are the plurality of medical images taken in a plurality of series included in the plurality of examinations.

Figure 2:
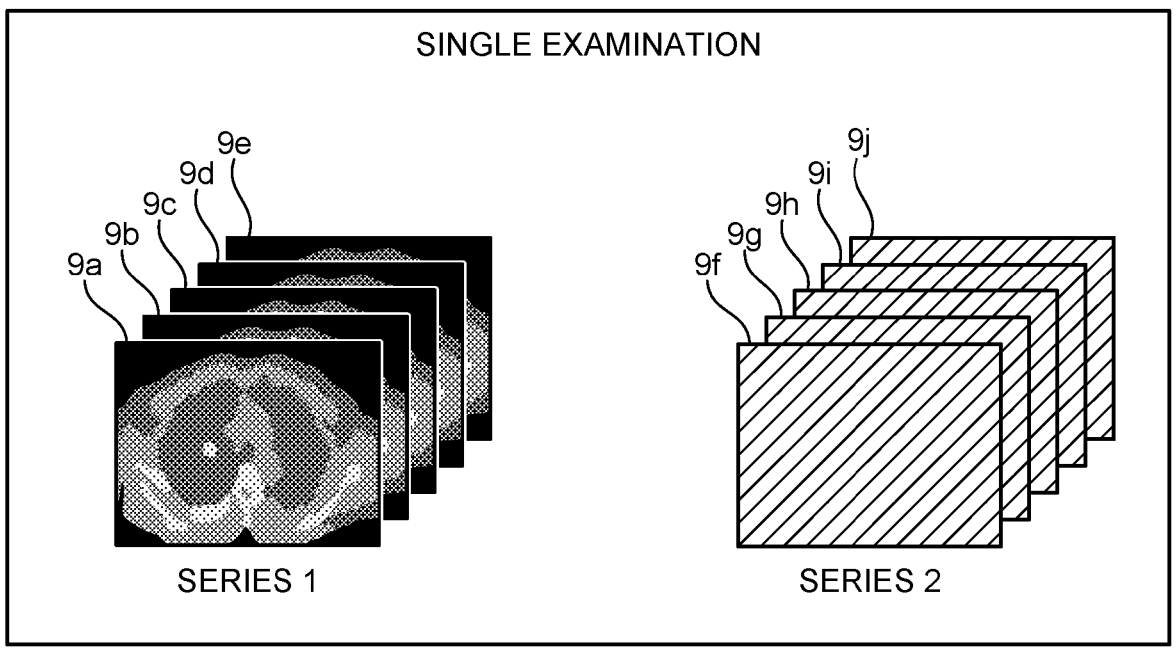
FIG. 2 is a drawing illustrating an example of concept of a plurality of medical images included in a single examination according to the first embodiment.

FIG. 2 is a drawing illustrating an example of concept of a plurality of medical images included in a single examination according to the first embodiment. With respect to the single examination, the medical image diagnosis apparatus 200 is configured to take a plurality of medical images in each of units called "series". In the example of FIG. 2, the single examination includes two series. Further, each of the series includes a plurality of medical images. In the example of FIG. 2, Series 1 includes medical images 9a to 9e, whereas Series 2 includes medical images 9f to 9j. In the following sections, when not particularly distinguished from one another, the medical images will simply be referred to as medical images 9.

The quantity of the series, the quantity of the medical images 9, and data formats of the medical images 9 illustrated in FIG. 2 are merely examples, and possible embodiments are not limited to these examples. For instance, the medical images 9 do not necessarily have to be two-dimensional images and may be three-dimensional volume data.

Further, together with the medical images 9, the obtaining function 151 is configured to obtain information about the examinations in which the medical images 9 were taken. The information about the examinations may be, for example, information such as the name of the patient being the examined subject, an ID number that makes the patient identifiable, the modalities used for the imaging, the examination dates and times, the quantity of the medical images taken in the examinations, examination numbers, descriptions of the examinations, and imaged ranges registered as additional information in DICOM. The information about the examinations may be registered with the individual medical images 9 as the additional information in DICOM or may be obtained as individual pieces of data.

Returning to the description of FIG. 1, the identifying function 152 is configured to identify an imaged range with respect to each of the plurality of examinations, on the basis of anatomical information of the plurality of medical images taken of the patient in the plurality of examinations.

On the basis of anatomical information rendered in a plurality of medical images 9 included in one of the plurality of series included in the plurality of examinations, the identifying function 152 is configured to identify an imaged range of the series. Further, the identifying function 152 is configured to identify a range obtained by combining together the imaged ranges of the plurality of series included in the single examination, as the imaged range of the examination.

The anatomical information denotes information about the position of a feature point related to an anatomical tissue such as a bone, an organ, or the like and may more specifically be referred to as anatomical landmark information. For example, an anatomical landmark is a local feature point included in an anatomical tissue such as "the lower end of a kidney", "the tip end of an n-th rib", or the like.

Figure 3:
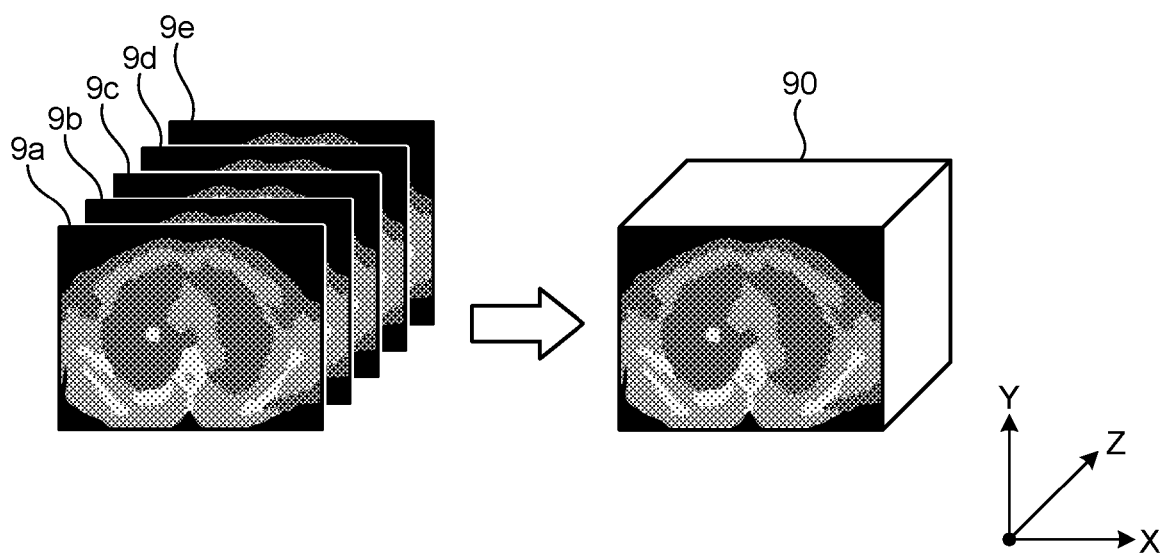
FIG. 3 is a drawing for explaining a process related to identifying an imaged range of each series according to the first embodiment.

FIG. 3 is a drawing for explaining a process related to identifying the imaged range of each of the series according to the first embodiment. As illustrated in FIG. 3, the identifying function 152 is configured to combine together the medical images 9a to 9e corresponding to the one series as one piece of volume data 90. After that, the identifying function 152 is configured to extract an anatomical landmark included in the volume data 90 through image processing. On the basis of the extracted anatomical landmark, the identifying function 152 is configured to identify the imaged range corresponding to the volume data 90. As for the method for extracting the anatomical landmark, it is possible to adopt any of publicly-known image processing techniques.

In the present embodiment, a range in the body axis direction of the patient in the volume data 90, i.e., in the Z direction in FIG. 3, will be referred to as the imaged range; however, the present definition of the imaged range is merely an example.

Also, with respect to the medical images 9f to 9j included in the other series, the identifying function 152 is configured to similarly identify an imaged range after combining the images together. In this situation, when the medical images 9 obtained from the medical image storage apparatus 500 is three-dimensional volume data, the combining process is unnecessary.

Further, the identifying function 152 is configured to determine the range ends of a range obtained by combining together all the imaged ranges identified in correspondence with the series, as an imaged range with respect to each of the units represented by the examinations.

Figure 4:
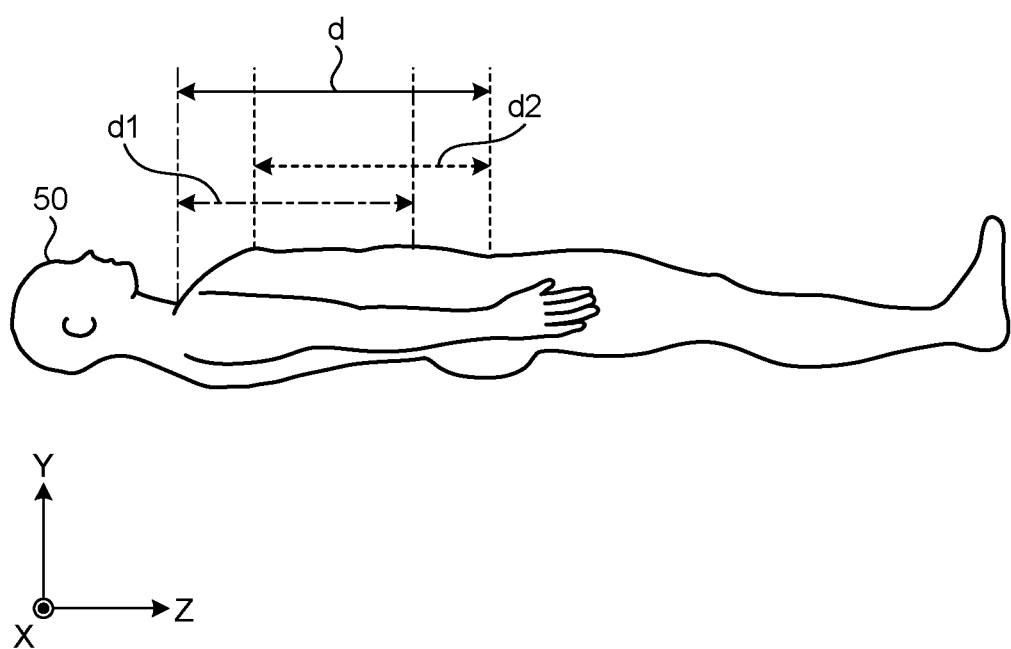
FIG. 4 is a drawing illustrating an example of a relationship between an imaged range of each series and an imaged range of an examination according to the first embodiment.

FIG. 4 is a drawing illustrating an example of a relationship between the imaged range of each of the series and the imaged range of the examination according to the first embodiment. In FIG. 4, for the sake of convenience in the explanation, imaged ranges d, d1, and d2 are indicated over a human body model 50 so as to be kept in correspondence therewith. The human body model 50 will be explained later in the description of the mapping function 153.

In the example of FIG. 4, the imaged range d1 is the imaged range corresponding to the medical images 9a to 9e in Series 1. Further, the imaged range d2 is the imaged range corresponding to the medical images 9f to 9j in Series 2.

As illustrated in FIG. 4, the identifying function 152 is configured to identify the imaged range d obtained by combining the imaged range d1 with the imaged range d2, as the imaged range of the examination including Series 1 and Series 2.

The identifying function 152 is configured to save the imaged range d identified with respect to each examination, into the memory 120, for example, so as to be kept in correspondence with the medical images 9. Alternatively, the identifying function 152 may save the imaged range d identified with respect to each examination, into the medical image storage apparatus 500, so as to be kept in correspondence with the medical images 9.

Returning to the description of FIG. 1, the mapping function 153 is configured to map an imaged range d with respect to each of a plurality of examinations onto the single human body model 50.

The human body model 50 schematically expresses a human body and may be referred to as a human body schema. In the present embodiment, the human body model 50 is a three-dimensional model having three dimensions. Although FIG. 4 illustrates the human body model 50 by using the image in which the human body is viewed from a side, it is also possible to display the model by using an image in which the human body is viewed from the front, because the human body model 50 is three-dimensional.

For example, the human body model 50 is stored in the memory 120 in advance. The mapping function 153 is configured to use one human body model 50 for each patient being an examined subject and to keep the imaged ranges of a plurality of examinations performed on the patient in correspondence with the single human body model 50. The mapping function 153 is configured to save, in the memory 120, the human body model 50 on which the imaged range of each of the examinations has been mapped, so as to be kept in correspondence with an ID number or the like capable of identifying the patient being the examined subject.

In this situation, the human body models 50 may have a standard shape or may have different shapes fitted to each person. In the present embodiment, it is assumed that the human body model 50 having a standard human body shape is used in common to a plurality of patients.

The display controlling function 154 is configured to cause the display 140 to display a list of information about the plurality of examinations and the human body model 50 on which the plurality of imaged ranges respectively corresponding to the plurality of examinations are mapped, so as to be kept in correspondence with each other. In the present embodiment, the display controlling function 154 is configured to cause the list and the human body model 50 to be displayed in the image interpretation viewer used by medical doctors and the like for interpreting medical images.

Figure 5:
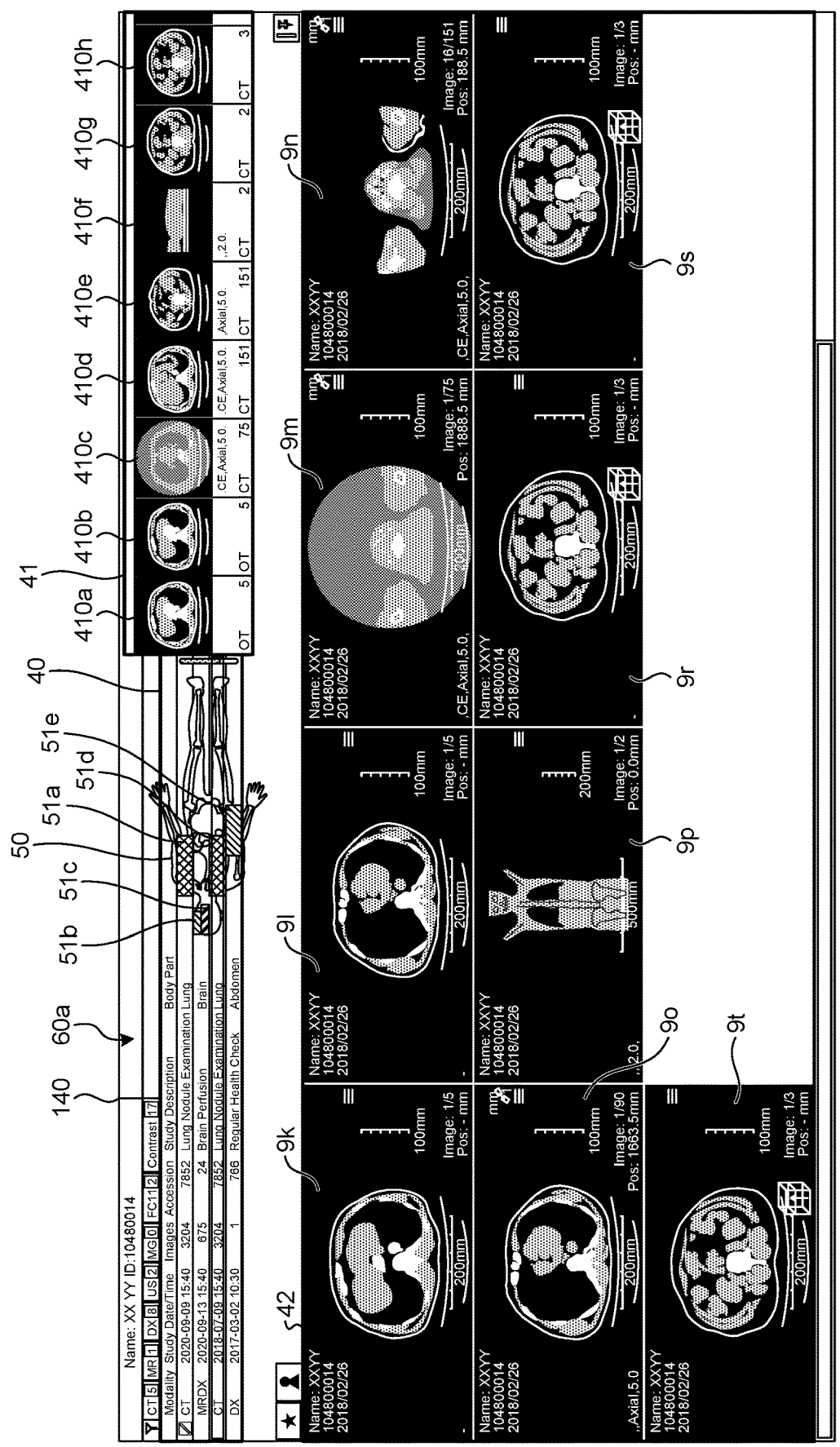
FIG. 5 is a drawing illustrating an example of an image interpretation viewer displayed on a display device according to the first embodiment.

FIG. 5 is a drawing illustrating an example of an image interpretation viewer 60a displayed on the display 140 according to the first embodiment. The image interpretation viewer 60a includes a list display area 40, a carousel area 41, and a medical image display area 42. The image interpretation viewer 60a is configured so that one screen is generated for each patient (examined subject).

The list display area 40 is a screen region displaying the list of the information about the plurality of examinations performed on the patient. The examinations written in the list are examinations that involve imaging of the patient. In the example of FIG. 5, the following items are displayed with respect to each of the examinations: the modality used for the imaging, the examination date and time ("Study Date/Time"), the number of medical images taken in the examination ("Images"), an examination number ("Accession"), a description of the examination ("Study Description"), and an imaged range ("Body Part") registered as the additional information in DICOM. The information about the examinations displayed in the list of FIG. 5 is merely an example. Information that can be displayed is not limited to these examples.

Further, the imaged ranges registered as the additional information in DICOM are based on a standard format where an arbitrary character string is input at the time of the imaging and therefore may not be the same as the actual imaged ranges. For example, even when a medical image was actually taken of a range from the chest to the abdomen, the additional information in DICOM may register "Lung" and may not indicate that the abdomen was imaged.

In the list display area 40, the display controlling function 154 is configured to cause the human body model 50 to be displayed while having mapped thereon the plurality of imaged ranges respectively corresponding to the plurality of examinations. As illustrated in FIG. 5, in each of the lines listing the information about the respective examinations, the display controlling function 154 is configured to display the human body model 50 and rectangular images 51a to 51e indicating the imaged ranges of the respective examinations, so as to be kept in correspondence with each other. The rectangular images 51a to 51e are examples of the range images in the present embodiment.

More specifically, the display controlling function 154 is configured to cause the rectangular images 51a to 51e to be displayed so as to be aligned with the positional arrangements of the lines showing the information about the respective examinations in the list, the rectangular images 51a to 51e being kept in correspondence with the positions corresponding to the imaged ranges in the human body model 50. As a result, the user is able to understand the imaged range of each of the examinations and to be able to easily compare the imaged ranges of the plurality of examinations with one another. For example, the rectangular image 51a indicating the imaged range of the CT examination being the first item in the list is displayed so as to extend from the chest to the abdomen of the human body model 50 and is also positioned in the first line of the list. In other words, the display controlling function 154 is configured to display the imaged range of each of the plurality of examinations so as to be kept in association with the corresponding position in the human body model 50, while using a display mode that makes it possible to compare among the plurality of examinations.

Further, the display mode of the rectangular images 51a to 51e may be varied in accordance with the pieces of information about the corresponding examinations. For example, in the example of FIG. 5, the display controlling function 154 may display the rectangular images 51a to 51e in mutually-different colors in correspondence with the modalities used for the examinations.

Further, although the human body model 50 in FIG. 5 presents the human body as viewed from the front, possible orientations of the human body model 50 are not limited to this example.

Further, the display controlling function 154 is configured to cause the image interpretation viewer 60a on the display 140 to display a plurality of medical images taken in an examination selected by the user.

The carousel area 41 is an image region displaying representative medical images 410a to 410h in correspondence with a plurality of series included in a single examination. In the example of FIG. 5, a CT examination, which is the third item from the top in the list display area 40, has been selected by the user. In this situation, the display controlling function 154 is configured to display, in the carousel area 41, the representative medical images 410a to 410h from the plurality of series included in the CT examination selected by the user.

In the carousel area 41, because glanceability is more prioritized than resolutions, the representative medical images 410a to 410h are displayed as thumbnail images that are reduced from the original medical images 9. For example, the representative medical images 410a to 410h may be made up of the first one of the medical images 9 from each series; however, the method for determining the representative medical images 410a to 410h is not particularly limited.

The medical image display area 42 is an image region displaying medical images 9k to 9s selected by the user. The sizes of the medical images 9k to 9s displayed in the medical image display area 42 are larger than the sizes of the representative medical images 410a to 410h displayed in the carousel area 41. For example, when the user has selected one of the series displayed in the carousel area 41, the display controlling function 154 is configured to cause the medical image display area 42 to display the medical images 9k to 9s included in the selected series.

In this situation, the image layout of the image interpretation viewer 60a in FIG. 5 is merely an example, and possible embodiments are not limited to this example.

Returning to the description of FIG. 1, the receiving function 155 is configured to receive various types of operations from the user via the input interface circuitry 130. For example, when the user clicks with the mouse on the list displayed in the image interpretation viewer 60a, the receiving function 155 receives the operation of selecting the examination corresponding to the clicked section.

Next, details of a flow in an imaged range identifying process performed by the medical image display apparatus 100 configured as described above will be explained.

Figure 6:
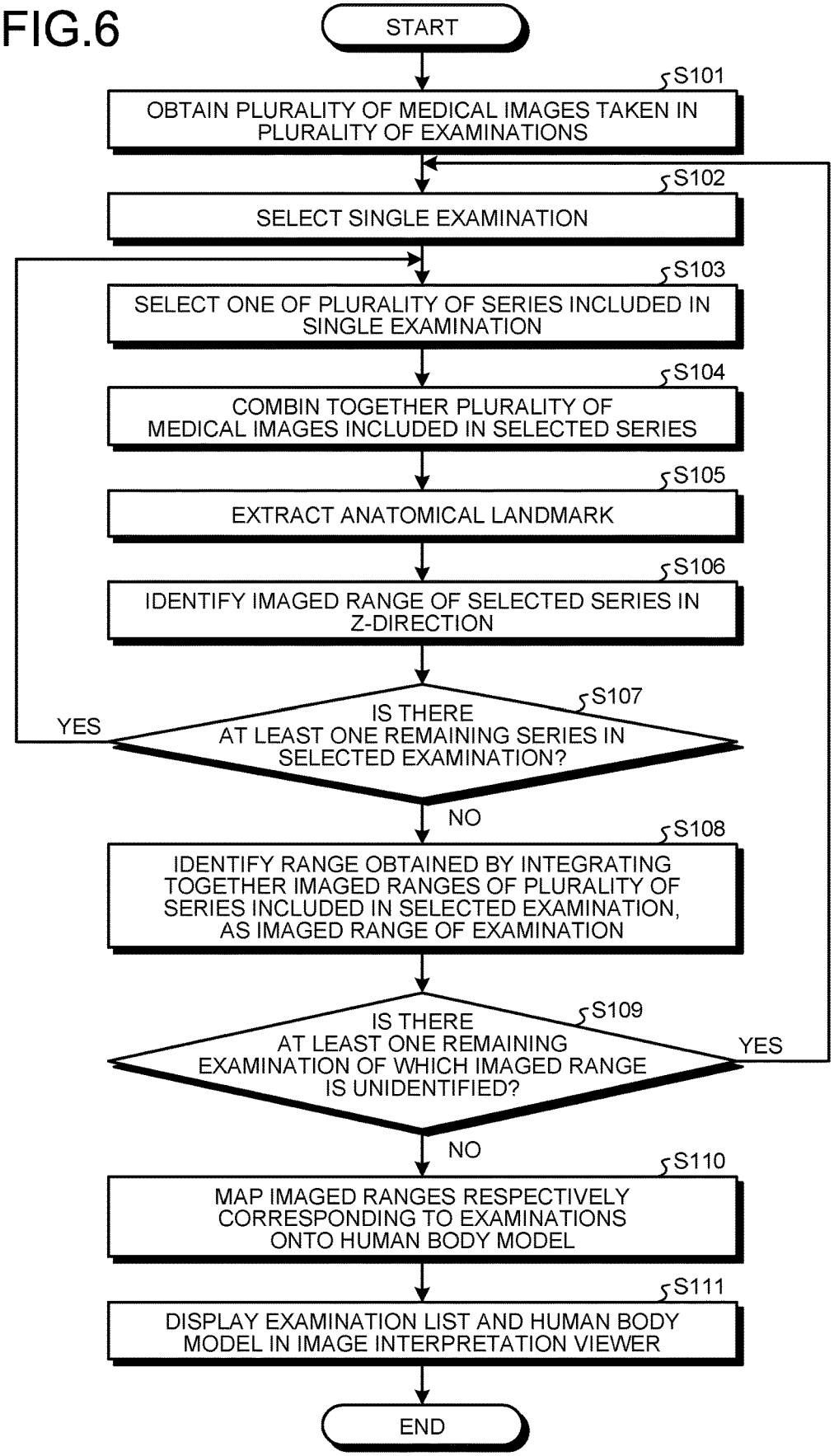
FIG. 6 is a flowchart illustrating an example of a flow in an imaged range identifying process according to the first embodiment.

FIG. 6 is a flowchart illustrating an example of the flow in the imaged range identifying process according to the first embodiment.

To begin with, the obtaining function 151 obtains the plurality of medical images 9 taken in the plurality of examinations (step S101).

After that, the identifying function 152 selects a single examination from among the plurality of examinations corresponding to the plurality of medical images 9 obtained by the obtaining function 151 (step S102). The standard for selecting the examination is not particularly limited, and the identifying function 152 may sequentially select examinations starting with the examination having the earliest date/time.

Subsequently, the identifying function 152 selects one of the plurality of series included in the selected single examination (step S103). The standard for selecting the series is not particularly limited, either.

After that, the identifying function 152 combines together the plurality of medical images 9a to 9e included in the one selected series as one piece of volume data 90 (step S104).

Subsequently, the identifying function 152 extracts an anatomical landmark from the volume data 90 (step S105).

On the basis of the type and the position of the anatomical landmark rendered in the volume data 90, the identifying function 152 identifies the imaged range of the selected series in terms of the Z direction (step S106).

Subsequently, with respect to the examination selected at step S102, the identifying function 152 judges whether or not there is at least one remaining series of which the imaged range has not been identified (step S107).

When there is at least one remaining series of which the imaged range has not been identified (step S107: Yes), the identifying function 152 repeatedly performs the processes at steps S103 through S106, until the imaged ranges of all the series included in the examination selected at step S102 are identified.

On the contrary, when there is no remaining series of which the imaged range has not been identified (step S107: No), because the imaged range identifying process has been completed with respect to all the series included in the selected examination, the identifying function 152 combines together the imaged ranges of the plurality of series included in the selected examination. The identifying function 152 identifies the combined range as the imaged range of the selected examination (step S108).

After that, the identifying function 152 judges whether or not there is at least one remaining examination of which the imaged range has not been identified (step S109).

When there is at least one remaining examination of which the imaged range has not been identified (step S109: Yes), the identifying function 152 repeatedly performs the processes at steps S102 through S108 until the imaged ranges of all the examinations obtained at step S101 are identified.

On the contrary, when there is no remaining examination of which the imaged range has not been identified (step S109: No), the mapping function 153 maps the imaged range of each of the examinations identified by the identifying function 152, onto the human body model 50 (step S110).

After that, as illustrated in FIG. 5, the display controlling function 154 causes the image interpretation viewer 60a to display the examination list and the human body model 50 on which the imaged range of each of the examinations is mapped, so as to be kept in correspondence with each other (step S111).

Although FIG. 6 illustrates the example in which the obtaining function 151 simultaneously obtains the medical images 9 taken in the plurality of examinations, the obtaining function 151 may obtain medical images 9 of each of the examinations at a time. In that situation, the imaged range identifying process and the mapping process of the identified result onto the human body model 50 may be performed with respect to each of the examinations at a time.

As explained above, the medical image display apparatus 100 according to the present embodiment is configured to cause the display 140 to display the list of the information about the plurality of examinations performed to image the patient in the plurality of examinations and the single human body model 50 onto which the plurality of imaged ranges corresponding to the plurality of examinations and having been identified on the basis of the anatomical information are mapped, so as to be kept in correspondence with each other. Consequently, by using the medical image display apparatus 100 according to the present embodiment, the user is able to easily understand and compare the imaged ranges corresponding to the various examinations performed on the patient.

In a comparison example, the imaged ranges registered with the medical images 9 as the additional information in DICOM may not be the same as the actual imaged ranges, as explained above. In contrast, the medical image display apparatus 100 according to the present embodiment is configured to identify the imaged ranges on the basis of the anatomical information actually rendered in the medical images 9. It is therefore possible to present the user with the imaged ranges having high accuracy. Further, the medical image display apparatus 100 according to the present embodiment is configured to keep the imaged ranges of the plurality of examinations in correspondence with the single human body model 50, instead of keeping the imaged ranges in correspondence with mutually-different human body models varied in association with medical images or medical examinations. It is therefore possible to clearly present the differences among the imaged ranges corresponding to the various examinations.

Further, in the list display area 40 for displaying the list of the information about the plurality of examinations, the medical image display apparatus 100 according to the present embodiment is configured to display the human body model 50, while the imaged ranges of the examinations written in the list are mapped thereon. Consequently, by using the medical image display apparatus 100 according to the present embodiment, the user is easily able to visually recognize the correspondence between the examinations written in the list and the imaged ranges mapped on the human body model 50.

Second Embodiment

In the first embodiment described above, the example was explained in which the medical image display apparatus 100 is configured to cause the human body model 50 to be displayed in the list display area 40 displaying the list of the information about the plurality of examinations. In a second embodiment, the human body model 50 is displayed in a position different from the position in the first embodiment.

The configuration of the medical image processing system S in the present embodiment is similar to the configuration in the first embodiment explained with reference to FIG. 1. Further, the configuration of the medical image display apparatus 100 according to the present embodiment is similar to the configuration in the first embodiment explained with reference to FIG. 1. Similarly to the first embodiment, the processing circuitry 150 of the medical image display apparatus 100 according to the present embodiment includes the obtaining function 151, the identifying function 152, the mapping function 153, the display controlling function 154, and the receiving function 155.

The obtaining function 151, the identifying function 152, the mapping function 153, and the receiving function 155 have functions similar to those in the first embodiment.

In the image interpretation viewer, the display controlling function 154 according to the present embodiment is configured to cause the human body model 50 to be displayed in the vicinity of the list of the information about the plurality of examinations.

Figure 7:
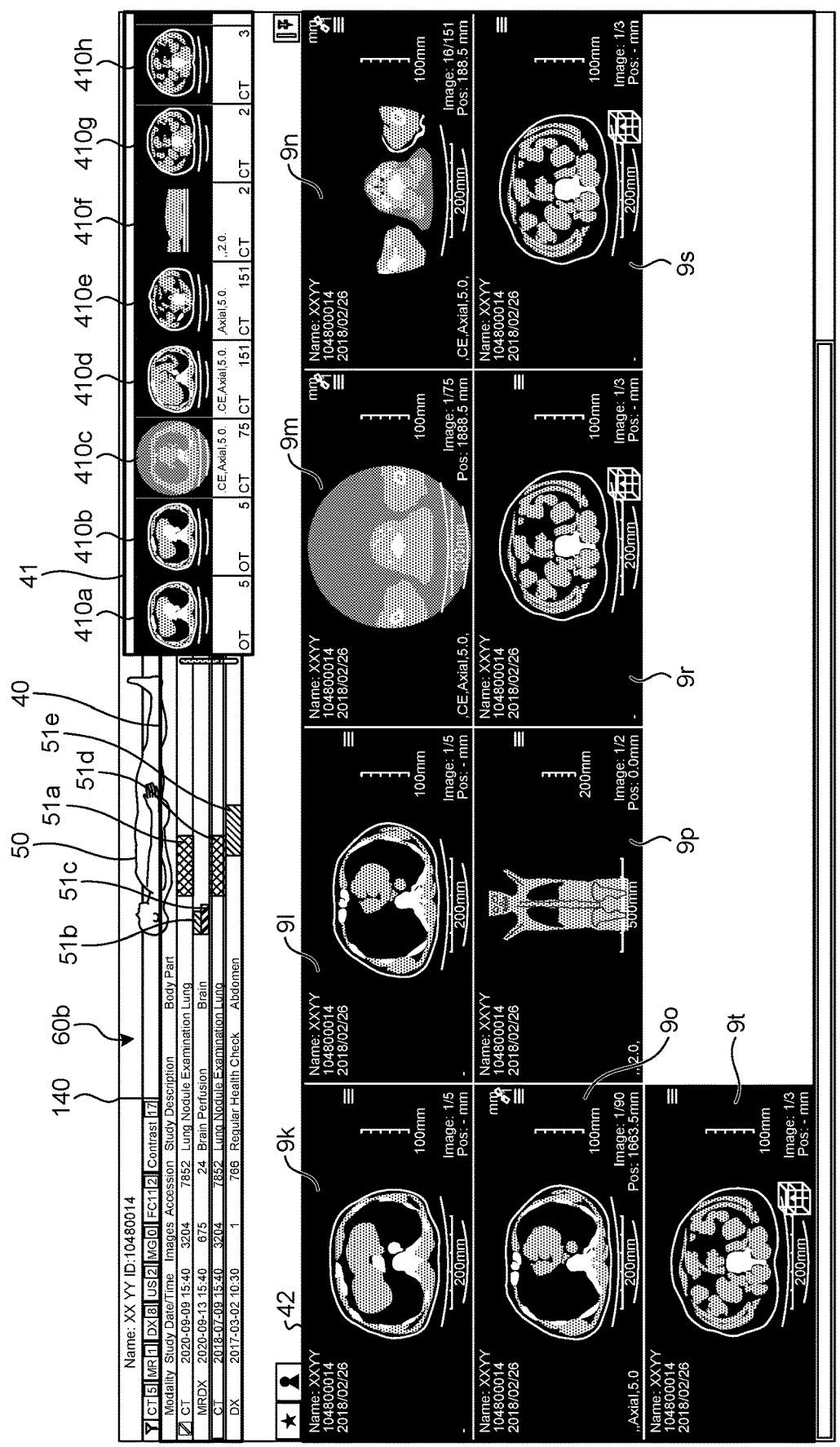
FIG. 7 is a drawing illustrating an example of an image interpretation viewer displayed on a display device according to a second embodiment.

FIG. 7 is a drawing illustrating an example of an image interpretation viewer 60b displayed on the display 140 according to the second embodiment. As illustrated in FIG. 7, in the image interpretation viewer 60b in the present embodiment, the human body model 50 is displayed in the vicinity of the list of the information about the examinations displayed in the list display area 40. In this situation, although FIG. 7 illustrates the example in which a part of the human body model 50 is included in the list display area 40, it is also acceptable to have the entirety of the human body model 50 positioned on the outside of the list display area 40.

In FIG. 7, the human body model 50 is displayed so that the human body is viewed from a side. It is because the display mode in which the human body is viewed from a side makes it easier to reduce the image region displaying the human body model 50, compared to the display mode in which the human body is viewed from the front as illustrated in FIG. 5.

In FIG. 7, the rectangular images 51a to 51e indicating the imaged ranges of the examinations are displayed in the lines of the list showing the information about the examinations, while being in the positions corresponding to the positions in the human body model 50 in terms of the body axis direction that correspond to the imaged ranges indicated by the rectangular images 51a to 51e. For example, the rectangular image 51a indicating the imaged range of the CT examination written as the first item in the list is displayed in the first line of the list, while being in the position corresponding to the range from the chest to the abdomen of the human body model 50.

In FIG. 5, the rectangular images 51a to 51e are displayed while being superimposed in the corresponding positions in the human body model 50. In contrast, in FIG. 7, the rectangular images 51a to 51e are displayed while being kept in correspondence with the positions in the human body model 50 in terms of the body axis direction that correspond to the imaged ranges, without overlapping with the human body model 50.

The medical image display apparatus 100 according to the present embodiment is configured to cause the human body model 50 to be displayed in the vicinity of the list of the information about the plurality of examinations in the image interpretation viewer 60b. Consequently, while achieving the same advantageous effects as those in the first embodiment, it is possible to clearly display both the list and the human body model 50, because the human body model 50 does not overlap with the list of the information about the plurality of examinations.

Third Embodiment

In a third embodiment, an image interpretation viewer is displayed by using a display layout different from the layouts in the first and the second embodiments described above.

The configurations of the medical image processing system S and the medical image display apparatus 100 in the present embodiment are similar to those in the first and the second embodiments. Similarly to the first embodiment, the processing circuitry 150 of the medical image display apparatus 100 according to the present embodiment includes the obtaining function 151, the identifying function 152, the mapping function 153, the display controlling function 154, and the receiving function 155.

The obtaining function 151, the identifying function 152, the mapping function 153, and the receiving function 155 have functions similar to those in the first embodiment.

Figure 8:
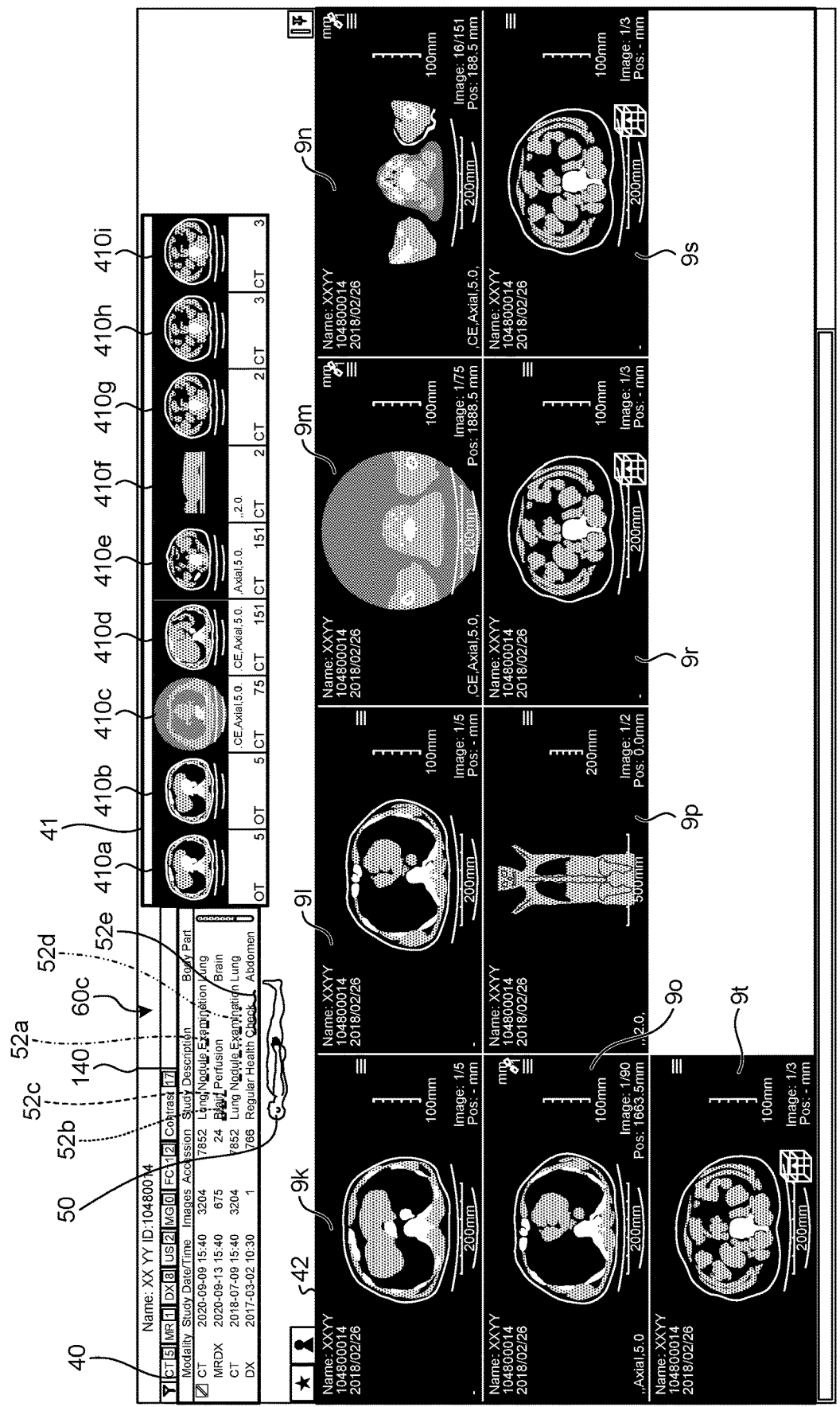
FIG. 8 is a drawing illustrating an example of an image interpretation viewer displayed on a display device according to a third embodiment.

FIG. 8 is a drawing illustrating an example of an image interpretation viewer 60c displayed on the display 140 according to the third embodiment. As illustrated in FIG. 8, the display controlling function 154 in the present embodiment is configured to cause the human body model 50 to be displayed in the vicinity of the list of the information about the examinations displayed in the list display area 40.

Further, the display controlling function 154 in the present embodiment is configured to cause underlines kept in correspondence with positions corresponding to the imaged ranges in the human body model 50 to be displayed in the lines showing the information about the examinations in the list. In the example of FIG. 8, the spans of underlines 52a to 52e drawn in the list of the examinations correspond to the imaged ranges in the body axis direction of the human body model 50. In FIG. 8, although the underlines 52a to 52e are drawn in the section "Study Description" showing the descriptions of the examinations, possible display locations of the underlines 52a to 52e are not limited to the locations in this example.

The underlines 52a to 52e require smaller image regions for the display, compared to the rectangular images 51a to 51e. It is therefore possible to keep the list display area 40 small. Further, in the present embodiment, the human body model 50 is also reduced compared to that in the second embodiment. Consequently, in the example in FIG. 8, it is possible to make the carousel area 41 larger than that in the examples in FIGS. 5 and 7.

Further, the display mode of the underlines 52a to 52e may be varied in accordance with the information about the corresponding examinations. For example, in the example of FIG. 8, the display controlling function 154 has the underlines 52a to 52e displayed in mutually-different shapes in correspondence with the modalities used for the examinations. Alternatively, the display controlling function 154 may be configured to vary the colors of the lines, instead of the shapes thereof.

Further, at the time of use, the user may be allowed to select any of the display layouts of the image interpretation viewers 60a to 60c presented in the first to the third embodiment illustrated in FIGS. 5, 7, and 8.

Fourth Embodiment

In the first to the third embodiments described above, displaying the imaged ranges by using the human body model 50 was explained. In a fourth embodiment, the identified imaged ranges are utilized as a search condition for the medical images 9.

Figure 9:
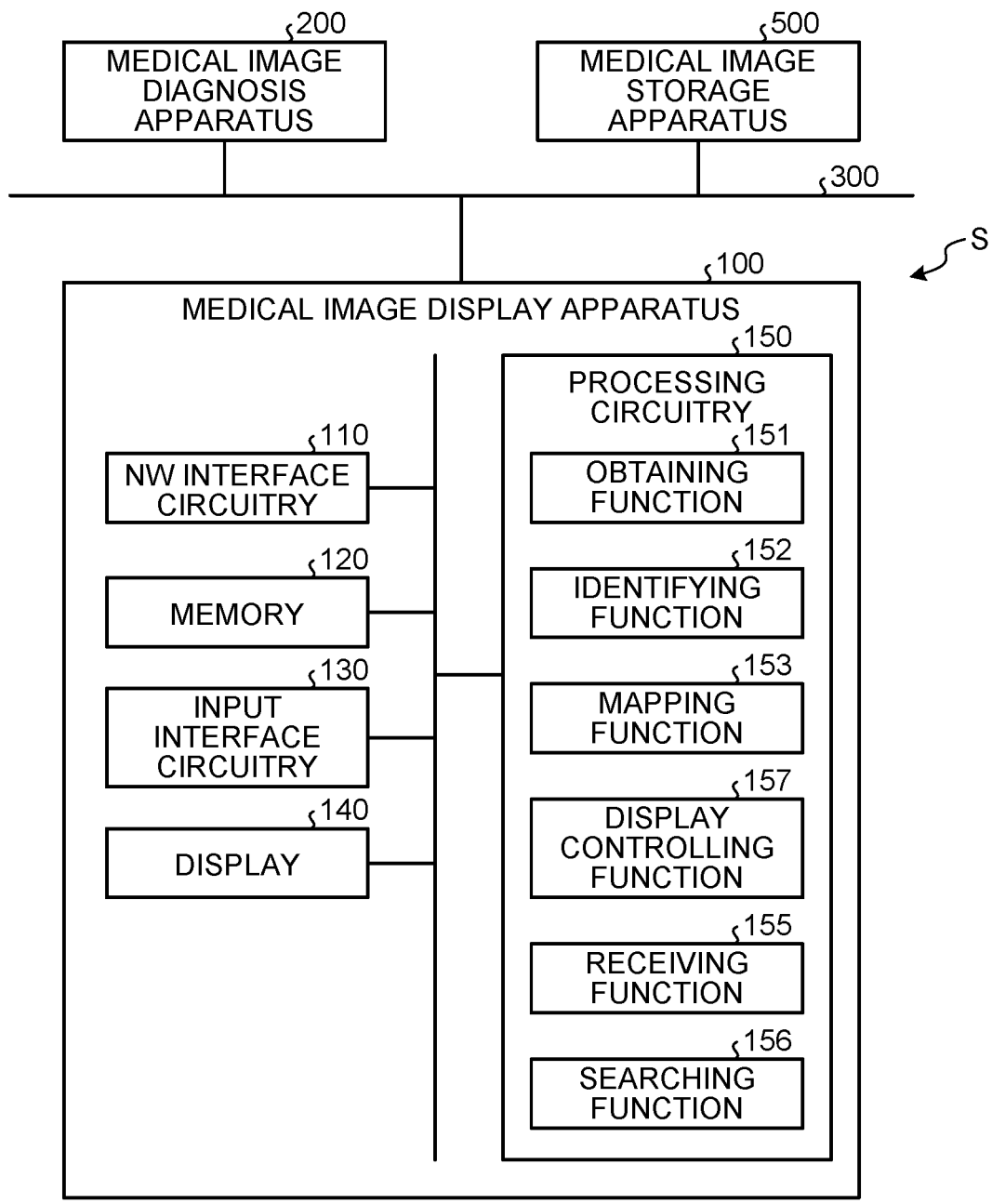
FIG. 9 is a drawing illustrating an example of an overall configuration of a medical image processing system according to a fourth embodiment.

FIG. 9 is a drawing illustrating an example of an overall configuration of the medical image processing system S according to the fourth embodiment. As illustrated in FIG. 9, the configuration of the medical image processing system S in the present embodiment is similar to the configurations in the first and the second embodiments.

Further, similarly to the first embodiment explained with reference to FIG. 1, the medical image display apparatus 100 according to the present embodiment includes the NW interface circuitry 110, the memory 120, the input interface circuitry 130, the display 140, and the processing circuitry 150.

The processing circuitry 150 of the medical image display apparatus 100 in the present embodiment includes the obtaining function 151, the identifying function 152, the mapping function 153, a display controlling function 157, the receiving function 155, and a searching function 156.

The obtaining function 151, the identifying function 152, the mapping function 153, and the receiving function 155 have functions similar to those in the first embodiment.

The searching function 156 is configured to search for one or more other medical images 9 kept in correspondence with the same imaged range as that of a medical image 9 selected by the user. What is searched for is the one or more medical images 9 taken of the same patient as the patient imaged in the selected medical image 9, in one or more other examinations different from the examination in which the selected medical image 9 was taken.

Further, when the difference between a plurality of imaged ranges is equal to or smaller than a prescribed threshold value, the searching function 156 is configured to determine that the plurality of imaged ranges are the same as each other. The value of the prescribed threshold value is not particularly limited. Further, the user may be able to set the prescribed threshold value.

Figure 10:
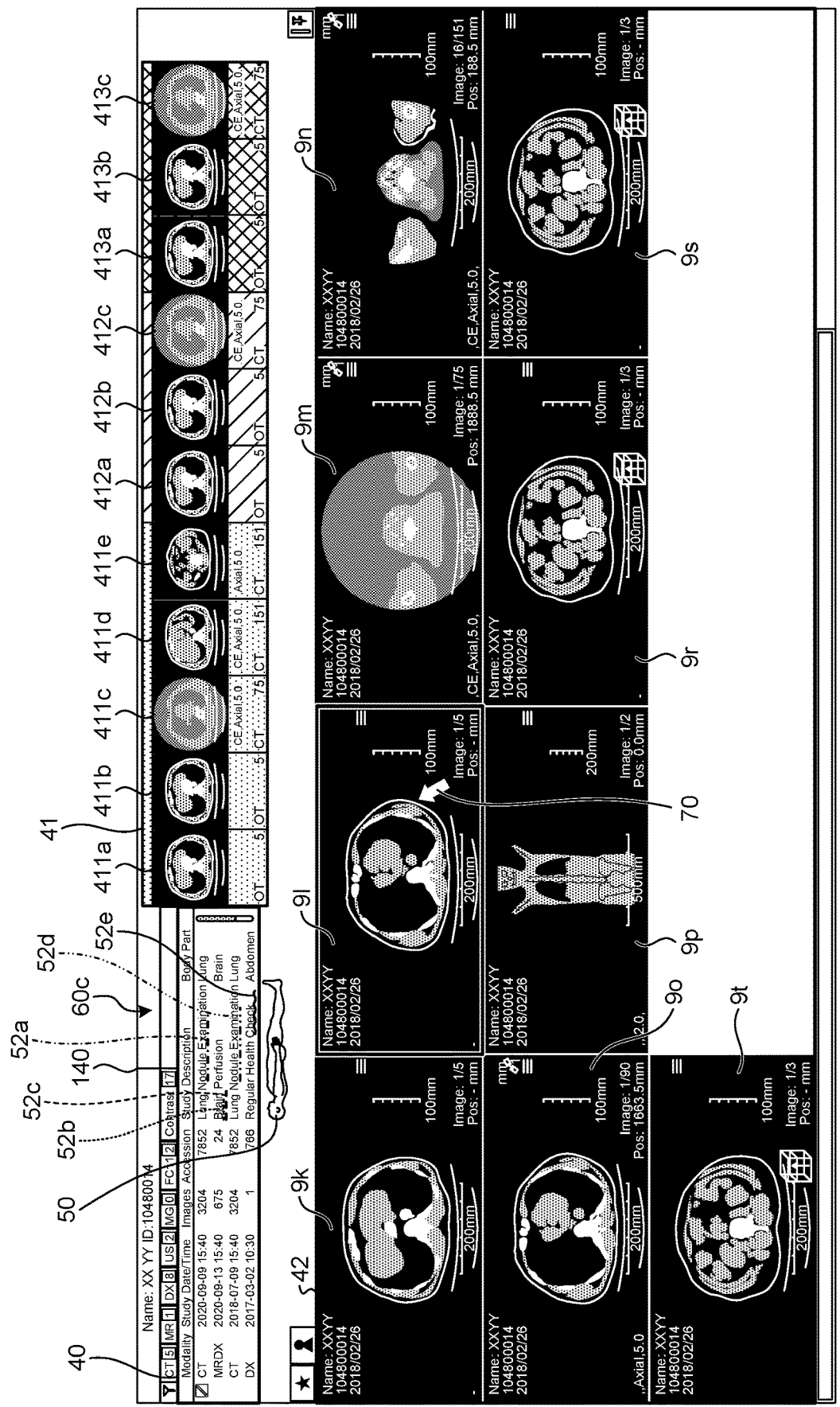
FIG. 10 is a drawing illustrating an example of an image search method according to the fourth embodiment.

FIG. 10 is a drawing illustrating an example of an image search method according to the fourth embodiment. Although FIG. 10 illustrates the display layout of the image interpretation viewer 60c explained in the third embodiment, it is also acceptable to adopt either of the image interpretation viewers 60a and 60b in the first and the second embodiments.

In the example in FIG. 10, from among the medical images 9k to 9t displayed in the medical image display area 42, a medical image 9l is selected by a user operation.

In FIG. 10, a pointer 70 of the mouse operated by the user is placed over the medical image 9l. For example, when the user clicks with the mouse while the pointer 70 is placed over the medical image 9l, the receiving function 155 is configured to receive the user operation to select the medical image 9l. In this situation, the searching function 156 is configured to search in the memory 120 or the medical image storage apparatus 500 for the one or more medical images 9 that are kept in correspondence with the same patient as the patient imaged in the medical image 9l and that were taken in one or more other examinations.

Because the imaged ranges have been identified in units of the examinations, the searching function 156 is configured to obtain, as a search result, the one or more medical images 9 taken in the one or more other examinations having the same imaged range as the medical image 9l. The searching function 156 is configured to send the medical images 9 obtained in the search to the display controlling function 157.

The display controlling function 157 according to the present embodiment is configured to cause the display 140 to display the medical images 9 kept in correspondence with the same imaged range as that of the medical image 9 selected by the user from among the other medical images 9 taken of the patient in the other examinations.

More specifically, the display controlling function 157 is configured to cause the display 140 to display the medical images 9 found in the search by the searching function 156 from the memory 120 or the medical image storage apparatus 500.

In the example of FIG. 10, the display controlling function 157 is configured to cause the carousel area 41 to display representative medical images 411a to 411e, 412a to 412c, and 413a to 413c in correspondence with the series that are kept in correspondence with the same patient as the patient imaged in the medical image 9l selected by the user and that are included in the one or more other examinations having the same imaged range as that of the medical image 9l.

The display controlling function 157 is configured to display the representative medical images 411a to 411e, 412a to 412c, and 413a to 413c in the carousel area 41 so as to be categorized in correspondence with the examinations. For instance, in the example of FIG. 10, the representative medical images 411a to 411e, the representative medical images 412a to 412c, and the representative medical images 413a to 413c are medical images taken in the series included in mutually-different examinations. In that situation, the display controlling function 157 may distinguish the examinations from one another by using different display modes, such as using mutually-different colors for the backgrounds of the representative medical images 411a to 411e, the representative medical images 412a to 412c, and the representative medical images 413a to 413c.

As explained above, the medical image display apparatus 100 according to the present embodiment is configured to receive the user operation to select one of the plurality of medical images 9 displayed on the display 140 and to cause the display 140 to display the medical images 9 kept in correspondence with the same imaged range as that of the medical image 9 selected by the user from among the other medical images 9 taken of the patient in the other examinations. Consequently, by using the medical image display apparatus 100 according to the present embodiment, the user is able to easily reference the other medical images 9 having the same imaged range, while achieving the same advantageous effects as those in the first embodiment.

For example, when interpreting images, the user may wish to compare medical images 9 taken in past examinations with another medical image 9 newly taken. In that situation, the medical image display apparatus 100 according to the present embodiment is capable of presenting the user with a past medical image 9 having the same imaged range as that of the newly-taken medical image 9. Consequently, it is possible to reduce the trouble of the user looking for the past medical image 9 to be compared and to thus make contribution to shortening overall image interpretation time.

Fifth Embodiment

In a fifth embodiment, a display layout is proposed in accordance with the imaged range of a medical image 9 selected by the user.

The configurations of the medical image processing system S and the medical image display apparatus 100 according to the present embodiment are similar to those in the fourth embodiment. Similarly to the fourth embodiment, the processing circuitry 150 of the medical image display apparatus 100 according to the present embodiment includes the obtaining function 151, the identifying function 152, the mapping function 153, the display controlling function 157, the receiving function 155, and the searching function 156.

The obtaining function 151, the identifying function 152, the mapping function 153, and the receiving function 155 have functions similar to those in the first embodiment.

Further, the memory 120 according to the present embodiment is configured to store therein a recommended display layout with respect to each of the categories of the imaged ranges.

For example, the categories of the imaged ranges are categories obtained by categorizing the imaged ranges identified by the identifying function 152 according to the positions thereof such as the "head", the "chest", the "abdomen", and the "chest and abdomen".

It is assumed, for example, that the categories of the imaged ranges are registered in the memory 120 while being kept in correspondence in advance with display layouts suitable for the imaged ranges belonging to the categories of the imaged ranges. Alternatively, at each medical institution, an administrator or the like may set the correspondence between the categories of the imaged ranges and the display layouts, for example.

While having functions similar to those in the fourth embodiment, the searching function 156 according to the present embodiment is configured to search in the memory 120 for a display layout kept in correspondence with the category of imaged ranges to which the imaged range of the medical image 9 selected by the user belongs.

Figure 11:
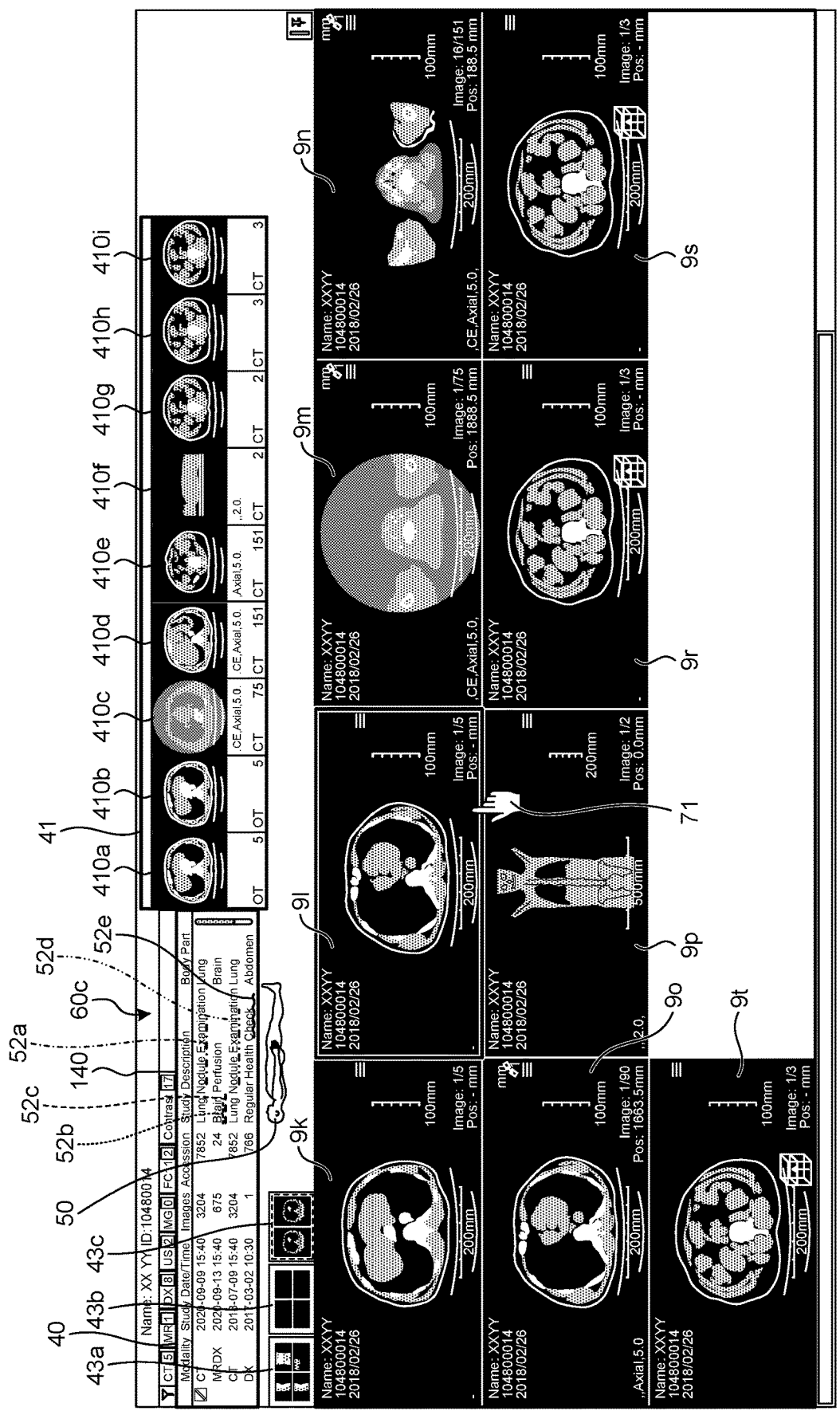
FIG. 11 is a drawing illustrating an example of a proposal for display layouts according to a fifth embodiment.

FIG. 11 is a drawing illustrating an example of a proposal for display layouts 43a to 43c according to the fifth embodiment. In the example of FIG. 11, a pointer 71 is placed over the medical image 9l. In other words, from among the medical images 9k to 9t displayed in the medical image display area 42, the medical image 9l is selected by the user operation.

In this situation, the searching function 156 is configured to search in the memory 120 for the display layouts 43a to 43c kept in correspondence with the category of imaged ranges to which the imaged range of the medical image 9l belongs. In FIG. 11, it is assumed that the category of the imaged range of the medical image 9l is the "chest and abdomen". The searching function 156 is configured to send the display layouts 43a to 43c kept in correspondence with the "chest and abdomen" and found in the search in the memory 120, to the display controlling function 157.

The display controlling function 157 is configured to cause the display 140 to display the display layouts 43a to 43c found in the search by the searching function 156 from the memory 120, as selectable options for a display layout. In the following sections, when not distinguished from one another individually, the display layouts 43a to 43c will simply be referred to as display layouts 43.

In the example of FIG. 11, the display controlling function 157 has the three types of display layouts 43a to 43c displayed above the medical image display area 42, by using a tab format. When the user has selected one of the display layouts 43a to 43c, the display controlling function 157 is configured to display the medical image 9l by using the selected one of the display layouts 43.

As explained above, the medical image display apparatus 100 according to the present embodiment is configured to cause the display 140 to display the selectable options for the display layout corresponding to the imaged range of the medical image 9 selected by the user. Consequently, the medical image display apparatus 100 according to the present embodiment is capable of assisting the user in selecting the display layout suitable for the image interpretation, while achieving the same advantageous effects as those in the first embodiment.

Modification Examples

In the fourth embodiment described above, the carousel area 41 displays, as explained with reference to FIG. 10, the representative medical images 411a to 411e, 412a to 412c, and 413a to 413c in the series kept in correspondence with the same imaged range as that of the medical image 9l selected by the user; however, methods for presenting the other medical images 9 kept in correspondence with the same imaged range as that of the medical image 9 selected by the user are not limited to the example illustrated in FIG. 10.

Figure 12:
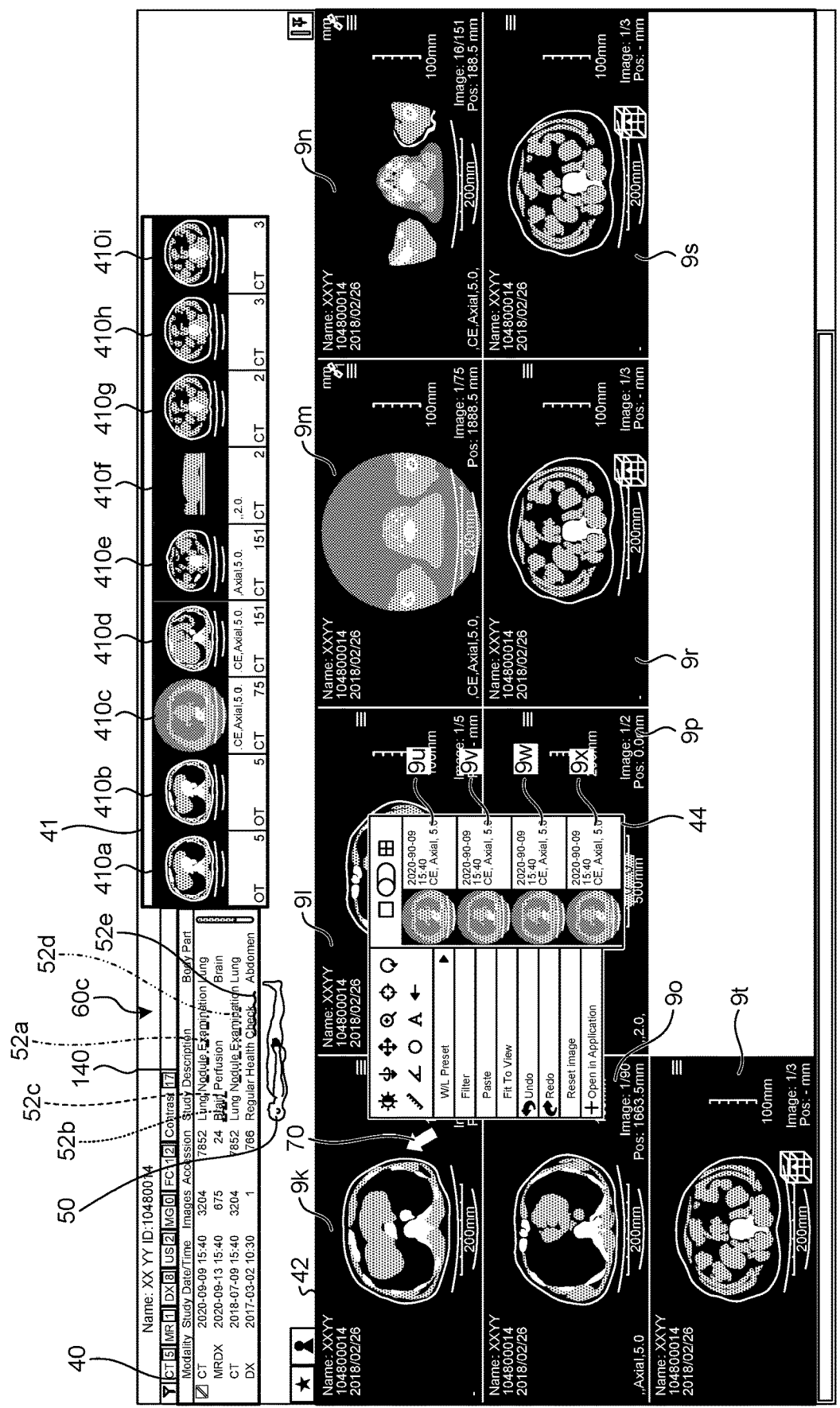
FIG. 12 is a drawing illustrating an example of an image search method according to a modification example.

FIG. 12 is a drawing illustrating an example of an image search method according to a modification example. In the example of FIG. 12, the pointer 70 of the mouse operated by the user is placed over the medical image 9k among the medical images 9k to 9t displayed in the medical image display area 42. When the user performs a right click with the mouse in this state, the receiving function 155 is configured to receive the user operation to select the medical image 9k and to cause a menu screen to be displayed.

In that situation, on a menu screen 44, the display controlling function 157 is configured to display other medical images 9u to 9x taken with the same imaged range as that of the medical image 9k. In this situation, on the menu screen 44, the medical images 9u to 9x are displayed as thumbnail images reduced from the original size.

When the user selects one of the medical images 9u to 9x displayed on the menu screen 44, the display controlling function 157 is configured to display the selected medical image 9 in the medical image display area 42.

Further, although FIG. 12 illustrates the example in which the display controlling function 157 displays the other medical images 9u to 9x on the menu screen 44, it is also acceptable to display, on the menu screen 44, the representative medical images 411a to 411e, 412a to 412c, and 413a to 413c in correspondence with the series.

Figure 13:
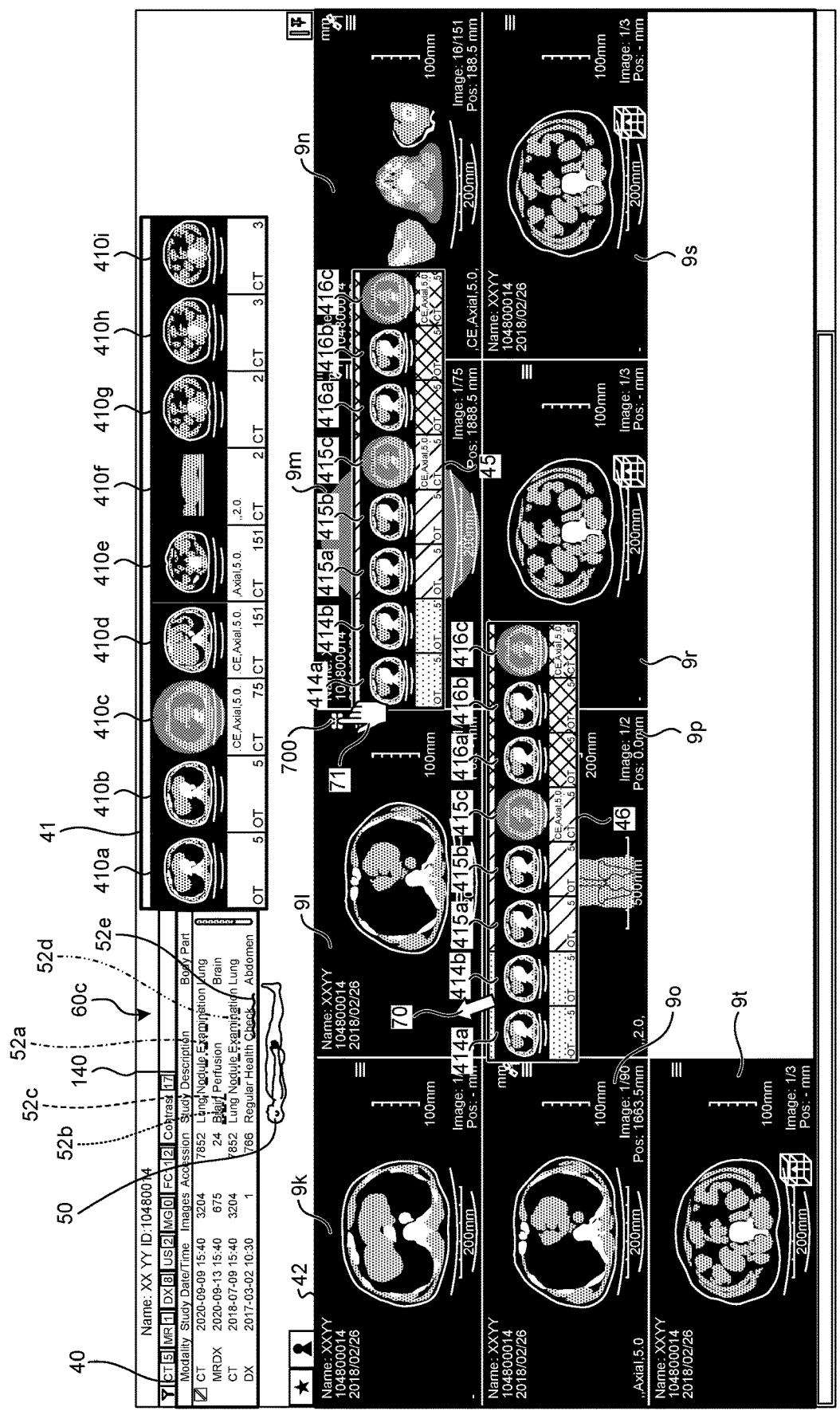
FIG. 13 is a drawing illustrating other examples of the image search method according to the modification example.

Further, FIG. 13 is a drawing illustrating other examples of the image search method according to the modification example. FIG. 13 illustrates two types of methods in the single drawing.

To begin with, in the first method, by pressing an icon image 700 displayed over the medical images 9k to 9t, the user may perform an operation to request a search for other medical images 9 kept in correspondence with the same imaged range as that of the medical image 9 corresponding to the icon image 700.

In the example of FIG. 13, the icon image 700 is displayed over the medical image 9l displayed in the medical image display area 42. Although the illustration of icon images 700 is omitted for the other medical images 9k and 9m to 9t, the display controlling function 157 is configured to cause an icon image 700 to be displayed with respect to each of the medical images 9k to 9t displayed in the medical image display area 42.

The icon images 700 are each an icon image used for receiving an operation to request a search for other medical images 9 kept in correspondence with the same imaged range as that of the medical image 9 corresponding to the icon image 700. When the user presses the icon image 700 positioned over the medical image 9l, the receiving function 155 is configured to receive the user operation to request a search for the other medical images 9 kept in correspondence with the same imaged range as that of the medical image 9l. In this situation, the searching function 156 is configured to search for the other medical images 9 kept in correspondence with the same imaged range as that of the medical image 9l.

After that, the display controlling function 157 is configured to cause a first popup screen 45 to display the representative medical images 414a, 414b, 415a to 415c, and 416a to 416c that are kept in correspondence with the same patient as the patient imaged in the medical image 9l selected by the user and that correspond to the series included in another examination having the same imaged range as that of the medical image 9l.

When the user selects one of the representative images 414a, 414b, 415a to 415c, and 416a to 416c displayed on the first popup screen 45, the display controlling function 157 is configured to display, in the medical image display area 42, the medical images 9 included in the series corresponding to the selected representative medical image.

Next, in the second method illustrated in FIG. 13, when the user clicks with the mouse on one of the medical images 9, the representative medical images 414a, 414b, 415a to 415c, and 416a to 416c are displayed on a second popup screen 46. In this situation, possible user operations are not limited to a click with the mouse, and it is also acceptable to perform a double click, a right click, or the like.

In the example of FIG. 13, when the user clicks with the mouse while the pointer 70 is placed over the medical image 9l, the display controlling function 157 is configured to cause the second popup screen 46 to display the representative images 414a, 414b, 415a to 415c, and 416a to 416c that are kept in correspondence with the same patient as the patient imaged in the medical image 9l and that correspond to the series included in the other examination having the same imaged range as that of the medical image 9l.

As explained in the present modification example, because the relevant medical images 9 are presented by using the various methods in response to the user operations, the user is able to easily reference the other medical images 9 having the same imaged range as that of the selected medical image 9.

A part or all of the functions of the medical image display apparatus 100 according to the embodiments described above may be realized in a cloud environment. Further, the various types of data handled in the present disclosure are, typically, digital data.

According to at least one aspect of the embodiments described above, the user is able to easily understand and compare the imaged ranges corresponding to the various examinations performed on the patient.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image display apparatus, comprising:
processing circuitry configured to
identify imaged ranges respectively corresponding to a plurality of examinations, based on anatomical information from a plurality of medical images taken of an examined subject in the plurality of examinations;
map the imaged ranges respectively corresponding to the plurality of examinations onto a single human body model; and
cause a display to display a screen including a first display area, a second display area, and a third display area, the first display area displaying a list of information about the plurality of examinations and the human body model on which the imaged ranges respectively corresponding to the plurality of examinations are mapped, so as to be kept in correspondence with each other, the second display area displaying a representative medical image of each of the plurality of examinations, and the third display area displaying a plurality of medical images included in one of the plurality of examinations corresponding to the representative medical image;
receive an operation to select a medical image from the plurality of medical images displayed on the third display area; and
cause the display to display a medical image kept in correspondence with a same imaged range as the selected medical image.

2. The medical image display apparatus according to claim 1, wherein the processing circuitry is further configured to cause the information about the examinations included in the list to be displayed so as to be kept in correspondence with positions in the human body model on which the imaged ranges corresponding to the examinations are mapped.

3. The medical image display apparatus according to claim 1, wherein the processing circuitry is further configured to cause the human body model to be displayed in the list or in a vicinity of the list.

4. The medical image display apparatus according to claim 1, wherein the processing circuitry is further configured to cause range images kept in correspondence with positions corresponding to the imaged ranges on the human body model to be displayed so as to be aligned with positional arrangements of lines showing the information about the examinations in the list.

5. The medical image display apparatus according to claim 1, wherein the processing circuitry is further configured to cause underlines kept in correspondence with positions corresponding to the imaged ranges on the human body model to be displayed in lines showing the information about the examinations in the list.

6. The medical image display apparatus according to claim 1, wherein
based on the anatomical information rendered in the plurality of medical images included in one of a plurality of series included in the plurality of examinations, the processing circuitry is further configured to identify an imaged range of the series, and
the processing circuitry is further configured to identify a range obtained by combining together imaged ranges of the plurality of series included in a single examination, as an imaged range of the examination.

7. The medical image display apparatus according to claim 1, wherein the processing circuitry is further configured to:
receive an operation from a user to select one of the examinations in the list; and
cause the display to display the plurality of medical images taken in the examination selected by the user.

8. The medical image display apparatus according to claim 7, wherein the processing circuitry is further configured to cause the display to display selectable options for a display layout corresponding to an imaged range of the medical image selected by the user.

* * * * *